(12) United States Patent
Lees et al.

(10) Patent No.: US 9,037,220 B2
(45) Date of Patent: May 19, 2015

(54) IMAGING DEVICE AND METHOD (75) Inventors: John Ernest Wyper Lees, Leicester (GB); Alan Christopher Perkins, Breaston Derbyshire (GB)

(73) Assignee: University of Leicester, Leicestershire (GB)

(*) Notice: Subject to any disclaimer, the term of this patent is extended or adjusted under 35 U.S.C. 154(b) by 1562 days.

(21) Appl. No.: 11/913,892

(22) PCT Filed: May 12, 2006

(86) PCT No.: PCT/GB2006/001773
§ 371 (c)(1),
(2), (4) Date: Jun. 12, 2008

(87) PCT Pub. No.: WO2006/123119
PCT Pub. Date: Nov. 23, 2006

(65) Prior Publication Data
US 2008/0242980 A1    Oct. 2, 2008

(30) Foreign Application Priority Data
May 16, 2005  (GB) .................................. 0509974.2

(51) Int. Cl.
*A61B 6/00*  (2006.01)
*G01T 1/161*  (2006.01)

(52) U.S. Cl.
CPC ...................................... *G01T 1/161* (2013.01)

(58) Field of Classification Search
CPC ................ G01T 1/2928; G01T 1/161; G01N 2021/8845; G01N 21/8806; A61B 1/042; A61B 6/4007; A61B 6/4258; A61B 6/482
USPC ......... 600/436, 431, 113, 129, 181, 182, 160, 600/109, 178, 117, 118, 473, 476; 348/162, 348/65
See application file for complete search history.

(56) References Cited

U.S. PATENT DOCUMENTS 4,679,068 A * 7/1987 Lillquist et al. ................. 348/33
5,591,976 A   1/1997 Berthold et al.
(Continued)

FOREIGN PATENT DOCUMENTS

JP    5312955 A    11/1993
JP    09218268 A   8/1997
(Continued)

OTHER PUBLICATIONS

Prout, D et al: "Detector concept for OPET, a combined Pet and optical imaging system" 2003 IEEE Nuclear Science Symposium Conference Record, Oct. 19-25, 2003, vol. 5.
(Continued)

*Primary Examiner* — Elmer Chao
(74) *Attorney, Agent, or Firm* — Fredrikson & Byron, P.A.

(57) ABSTRACT

A device (1) for use in imaging a subject using both light and gamma rays emanating from the subject, the device including: a first sensor means (2) responsive to light received thereby from the subject to generate first signals (6) for use in forming a first image (10) of the subject; a second sensor means (3) responsive to gamma rays received thereby from the subject to generate second signals (7) for use in forming a second image (11) of the subject and arranged to receive gamma rays from the subject which have passed from the subject through the first sensor means before reaching the second sensor means.

23 Claims, 4 Drawing Sheets (56) References Cited

U.S. PATENT DOCUMENTS

| | | |
|---|---|---|
| 6,081,739 A | 6/2000 | Lemchen |
| 6,380,541 B1 | 4/2002 | Laine |
| 6,643,538 B1 | 11/2003 | Majewski et al. |
| 2001/0030744 A1* | 10/2001 | Chang .................. 356/237.3 |
| 2002/0036269 A1* | 3/2002 | Shahar et al. ............ 250/370.1 |
| 2002/0087079 A1* | 7/2002 | Kaufman et al. ............ 600/436 |
| 2003/0118155 A1 | 6/2003 | Ueno |
| 2003/0218134 A1 | 11/2003 | Matoba |
| 2004/0152975 A1 | 8/2004 | Blevis |
| 2005/0215873 A1 | 9/2005 | Peter |

FOREIGN PATENT DOCUMENTS

| | | |
|---|---|---|
| JP | 2001215278 A | 8/2001 |
| JP | 2004085250 A | 3/2004 |
| WO | WO/02/46791 A1 | 6/2002 |

OTHER PUBLICATIONS

Lees, John E. et al.: "The High Resolution Gamma Imager (HGRI): a CCD based camera for medical imaging" Elsevier Science, 2001.

* cited by examiner

IMAGING DEVICE AND METHOD

RELATED APPLICATIONS

This application claims priority to International Application No. PCT/GB2006/001773 filed 12 May 2006, and to British Application No. 0509974.2, filed 16 May 2005, the teachings of all of which are incorporated herein by reference.

The present invention relates to a method and device for imaging a subject using non-visible radiation penetrating the subject. In particular, though not exclusively, the non-visible penetrating radiation may be gamma radiation or hard X-ray radiation or the like.

The imaging of subjects using high-energy penetrating electromagnetic radiation (e.g. gamma radiation or hard X-rays) concerns the generation of an image of parts of the subject which are otherwise not visible to the naked eye. For example, when the high-energy penetrating radiation in question emanates from a location within the body of a subject hidden from view, the penetrating nature of the high-energy radiation may enable the radiation to pass through the body of the subject and to emanate from the subject towards a suitable imaging device responsive to the high-energy radiation to produce a viewable image based on that received radiation. This technique is commonly employed in the imaging of patients for medical purposes, and for the purposes of non-destructive testing of articles or objects as follows.

In each case, for example, a radioactive substance such as a radionuclide is placed within the internal part of the subject (e.g. the patient or the object being tested) via a "tracer" selected to most effectively convey the radionuclide to the required internal location within the subject. When at the desired location, high-energy radionuclide emissions (e.g. gamma rays or hard X-rays) emitted by the radionuclide within the tracer may pass through the tissues or materials of the subject in question, emanate from the subject and be received by an imaging device thereby enabling the imaging device to form an image of those internal parts of the imaged subject containing the tracer. This method, when applied to medical imaging of patients, is commonly referred to as scintigraphy of autoradiography.

Unfortunately, an image produced according to the high-energy radiation received by the imaging device will only permit the production of an isolated and apparently disembodied image of the tracer-bearing internal component of the subject in question. That is to say, no concurrent image of the body of the subject as a whole, for example the visible surface of the subject behind which the tracer-bearing subject component is located, can be produced in this way using the received high-energy radiation alone.

This shortcoming of existing imaging systems can often render the full and proper interpretation of a hidden tracer-bearing internal component problematic in the sense that the true location, position and orientation of the internal component relative to the visible surface of the subject cannot be readily determined from the image alone. In order to ascertain this information complicated calibrations are required with respect to static coordinate systems in order that a user may infer the position of the imaged internal component based on a knowledge of the position of the imaging device relative to the subject being imaged. This is costly and troublesome to implement, and is often highly inconvenient.

The present invention aims to address at least some of the aforementioned shortcomings of the prior art.

At its most general the present invention proposes a method and device for imaging a subject using both light and non-visible penetrating radiation for imaging from the same viewpoint a common scene containing an image subject. The invention proposes employing a first sensor for light imaging and a second sensor for "looking" through the first sensor at the subject for imaging the subject using non-visible penetrating radiation that has passed through the first sensor.

The imaging may simultaneously use both light and non-visible penetrating radiation emitted concurrently from the image subject. The non-visible penetrating radiation may be gamma radiation or hard X-ray radiation (or the like), and the light may be visible radiation (i.e. visible to humans) or may be Ultra Violet light or Infra-Red light. Thus, in an imaging device, the present invention proposes, for example, forming an image from light received by the device from the subject and forming another image from non-visible penetrating radiation co-propagating with the light and received by the device, from the subject, simultaneously with receiving the light.

Preferably, both received light and penetrating radiation define a common field of view "seen" by the device, wherein a field of view of the device according to light has substantially no parallax relative to a common field of view of the device according to non-visible penetrating radiation, and each of these fields of vision includes the location of the image subject. Accordingly, the present invention may be used to generate simultaneous parallax-free images of a given subject in terms of both the view "seen" by the device using light and the view "seen" by the device using non-visible penetrating radiation. A composite image may then be generated comprising both views in which the position of an otherwise non-visible subject is readily apparent relative to the visible parts of the subject simultaneously represented in the same one composite image and representing a view from a common single viewpoint.

In a first of its aspects the present invention may provide a device for use in imaging a subject using both light and gamma rays emanating from the subject, the device including: a first sensor means responsive to light received thereby from the subject to generate first signals for use in forming a first image of the subject; a second sensor means responsive to gamma rays from the subject to generate second signals for use in forming a second image of the subject and arranged to receive gamma rays from the subject which have passed from the subject through the first sensor means before reaching the second sensor means. Preferably, the first sensor means is substantially transparent to gamma rays from the subject.

The first sensor means may have a sensing/imaging plane upon which light impinges to produce the first signals, and the second sensor means preferably has a sensing/imaging plane at which the second signals are produced (or derive) and the first and second sensing planes are preferably substantially parallel and preferably at least partially overlapping.

For example, the first sensor means preferably possesses an optic axis which is substantially parallel with (or coincident, or coaxial, with) the optic axis (or the equivalent thereof) of the second sensor means. The optic axis may refer to an axis, path or direction extending from a sensor through the centre of the field of vision of the sensor.

For example, the second sensor may have a field of vision and be responsive to gamma rays received thereby from the subject within the field of vision to generate second signals for use in forming a second image of the subject and the first sensor means may be positioned within the field of vision of the second sensor means, the second sensor means being responsive to gamma rays within the field of vision which have passed from the subject through the first sensor means before reaching the second sensor means.

The first sensor means is preferably dimensioned and arranged to impart substantially no attenuation of gamma rays which are incident thereupon from the subject and propagating towards the second sensor means in the field of vision thereof.

The first sensor means and the second sensor means are preferably arranged to receive light and gamma rays, respectively, which propagate from the subject (e.g. concurrently) upon substantially coincident (e.g. coaxial) paths such that the first sensor means has a field of vision at least a part of which corresponds with at least a part of the field of vision of the second sensor means.

The first and second sensor means each has a field of vision, and the second sensor means and the first sensor means may be co-aligned so as to share substantially a common (e.g., identical) field of vision.

The second sensor means preferably has an aperture delimiting (e.g., acting as an aperture stop) the field of vision thereof, and the first sensor means preferably substantially covers the whole of the aperture.

The first sensor means may be attached to the second sensor means. It may be directly attached to the second sensor means, e.g. preferably by mechanical attachment or connection, or alternatively by bonding with or without a bonding agent. The first sensor means may be formed upon the second sensor means. However, it is preferred that the first sensor means is detachably attached/connected to the second sensor means e.g. by mechanical means thereby allowing the first sensor means to separated from the second sensor means with ease for the purposes of repair, servicing or replacement of either the first or second sensor means.

The first sensor means preferably includes a solid-state pixel sensor device, such as a charge coupled device (CCD) or MOS or CMOS sensor array. These may be active pixel devices.

The second sensor means may include a semiconductor sensor device, e.g., semiconductor pixel sensor array in which semiconductor parts of the second sensor are responsive to gamma-rays to generate the second signals, or signals from which the second signals are derivable. Semiconductor materials responsive to gamma-rays to produce a measurable e.g., electrical, signal may be such as are readily available to the skilled person. For example, Silicon, GaAs, CdTe are examples of suitable such semiconductor materials.

The second sensor means may include a solid-state pixel sensor device, such as a charge coupled device (CCD) or MOS (Metal Oxide Semiconductor) or CMOS sensor array arranged to directly detect X-rays and/or gamma rays incident upon the pixel sensor parts thereof. These may be active pixel devices. Direct gamma-ray detection by semiconductor sensor devices as described above is to be distinguished from indirect gamma-ray sensor devices employing scintillation methods whereby a pixel sensor array is arranged to detect scintillation induced within a scintillator layer by incident gamma rays. Direct gamma ray detection methods and means obviate the need for a scintillation means since they are arranged to directly receive and respond to such rays.

The second sensor means may include an array of pixel sensors fabricated from Si, GaAs or CdTe, and forming an active sensing layer/array (e.g. about 50-300 microns thick, preferably 50-100 microns thick) arranged upon a p+ substrate (e.g. about 500 to 600 microns thick) and being responsive to gamma rays to produce a detectable electrical signal corresponding to, or for use in generating, the aforesaid second signals. The range of photon energies to which the second sensor means is responsive may be increased by increasing the thickness of the active sensing layer of the sensor so as to enable it to stop photons of higher energy. The opposite effect may be produced by decreasing the active sensing layer thickness. Alternatively, or additionally, semiconductor materials which are more absorbent of higher energy X-rays or gamma rays may be employed with or without increasing the thickness of the absorbing layer. For example, CdTe may be more absorbent of high energy photons than is GaAs which, in turn, may be more absorbent of high energy photons than is Si.

Of course, the second sensor means may employ indirect gamma-ray detection as an alternative to direct detection. The second sensor means may include a scintillator means responsive to gamma rays from the object by scintillation, and a scintillation sensor means arranged to generate said second signals in response to said scintillation. The scintillation sensor means may be a solid-state pixel sensor device (e.g. active pixel devices) such as e.g. a charge coupled device (CCD) or CMOS sensor array.

The second sensor means preferably includes a collimation means arranged between the first sensor means and (e.g. the sensing array of) the second sensor means to collimate gamma rays which have passed from the subject through the first sensor means before reaching the light sensor means of the second sensor means.

Where indirect sensing is employed, the second sensor means preferably includes a collimation means arranged between the first sensor means and the scintillator means of the second sensor means to collimate gamma rays which have passed from the subject through the first sensor means before reaching the light sensor means of the second sensor means.

The collimator means may be one or more aperture masks. The collimation means may comprise sheet or block of gamma-ray absorbent material (e.g. Lead (Pb) or Tungsten) into which extends an array of parallel collimation holes or channels passing from one side of the sheet or block through to an opposite side thereof through which gamma-rays may pass unimpeded. The thickness of the sheet or block is selected such that gamma-rays impinging upon a part of the collimator are substantially impeded (e.g., scattered or absorbed) thereby. Thus, gamma-rays not propagating through a hole or channel in a direction substantially or approximately parallel to the axis of the hole/channel will be filtered from the gamma-rays reaching the sensor array of the second sensor means.

For example, a collimator may be manufactured from a layering of a plurality (e.g. seven) such sheets with mutually aligned channels or holes collectively forming an array of parallel collimation channels. In one embodiment, a plurality of sheets each having an array of small diameter holes (e.g. about 1 mm diameter or less) separated by a small inter-hole pitch (e.g. 1.3 mm pitch) giving an overall thickness of the order of between about 10 mm and several tens of mm. This type of arrangement is found to produce gamma-ray images of relatively high spatial resolution due to the high density and small gauge of collimation channels.

For example, a collimator, being sensitive to low-intensity gamma-ray sources, may be fabricated from a plurality of aligned sheets each having an array of larger diameter holes (e.g. 2 mm or more) separated by a larger inter-hole pitch (e.g., 2.5 mm pitch). This type of arrangement is found to produce gamma-ray images from sources of relatively low intensity due to the higher aperture of the collimation channels.

Geometric sensitivities of about $1 \times 10^{-4}$ and $1 \times 10^{-2}$ for the high spatial resolution and the high sensitivity collimators respectively may be provided.

The device may include control means for controlling the first and second sensor means to generate (preferably simultaneously) respective first and second signals in response to (e.g. concurrent) light and gamma rays from said subject, signal processing means to generate image data from the (e.g. concurrent) first and second data signals representing an image composite of both the image of the subject according to light and concurrently according to gamma radiation.

The second sensor means (or the scintillation sensor means of the second sensor means, where scintillation is employed) preferably includes a solid-state pixel sensor array, and processing means arranged to receive an input from the pixel sensor array being configurable to operate in a photon counting mode to generate said second signal according to said input (e.g. resulting from scintillation or direct gamma ray receipt by the pixel sensor array).

Photon counting mode means that every gamma-ray reaching the second detector means is detected and the position and energy of the incident photon is preferably recorded. With this complete information the second sensor means may discriminate against gamma rays outside the energy range of interest. This leads to sharper and more accurate images.

In a second of its aspects, the present invention may provide a stereoscope for use in imaging a subject stereoscopically including: a first device according to the invention in its first aspect for imaging the subject; a second device according to the invention in its first aspect for imaging the subject (preferably concurrently) with the first device being separate from the first device and arranged such that the field of vision of the second sensor means of the second device differs from the (e.g. concurrent) field of vision of the second sensor means of the first device by a finite predetermined parallax; signal processing means to generate image data from the (e.g. concurrent) first and second signals of both the first and second device representing a three-dimensional (3D) stereoscopic composite view of the image of the subject both according to light and concurrently according to gamma radiation.

In a third of its aspects that present invention may provide a method of imaging a subject using both light and gamma rays emanating from the subject, the method including: detecting light from the subject with a first sensor means and therewith generating first signals for use in forming a first image of the subject; detecting with a second sensor means gamma rays from the subject which have passed from the subject through the first sensor means before reaching the second sensor means and therewith generating second signals for use in forming a second image of the subject.

The method may include arranging the first sensor means and the second sensor means to receive light and gamma rays, respectively, which propagate from the subject (e.g. concurrently) upon substantially coincident paths such that the first sensor means has a field of vision at least a part of which corresponds with at least a part of the field of vision of the second sensor means.

The method may include co-aligning the first and second sensor means so as to share substantially a common field of vision.

The method may include providing the second sensor means with an aperture delimiting the field of vision thereof, and substantially covering the whole of the aperture with the first sensor means.

In the method, the first sensor means may be attached to the second sensor means. It may be directly attached, it may be bonded (with or without a bonding agent) or it may be formed upon the second sensor means.

The method may include detecting said gamma rays with said second sensor by detecting scintillations within a scintillator means thereof responsive to gamma rays from the subject by scintillation, and generating said second signals in response to said scintillation.

The method may include collimating gamma rays which have passed from the subject through the first sensor means before being detected by the second sensor means.

The method may include controlling the first and second sensor means to generate respective first and second signals (preferably concurrently) in response to light and gamma rays from said subject, and (preferably concurrently) generating image data from the first and second data signals representing an image composite of the image of the subject both according to light and concurrently according to gamma radiation.

In a fourth of its aspects, the present invention may provide a method of imaging a subject stereoscopically including: in a first step generating said first and second signals according to the method of the invention in its third aspect for imaging the subject; in a second step (preferably concurrent with the first step) generating said first and second signals according to the method of the invention in its third aspect for imaging the subject such that the field of vision of the image associated with of the second step differs from the field of vision of the image associated with the first step by a finite predetermined parallax; generating image data (preferably concurrently) from the first and second signals generated in both the first and second steps representing a three-dimensional (3D) stereoscopic composite view of the image of the subject both according to light and concurrently according to gamma radiation.

The term "gamma rays" includes electromagnetic radiation in the energy range of about 2 keV to 300 keV or above. This includes X-Rays such as "hard" X-Rays.

There now follow non-limiting examples of the invention with reference to the accompanying drawings in which:

FIG. 4 schematically illustrates the nature of the composite image which the imaging devices of both FIG. 1 and FIG. 3 are arranged to produce in use;

In the following description, like articles are assigned like reference symbols for the sake of consistency.

Figure 1:
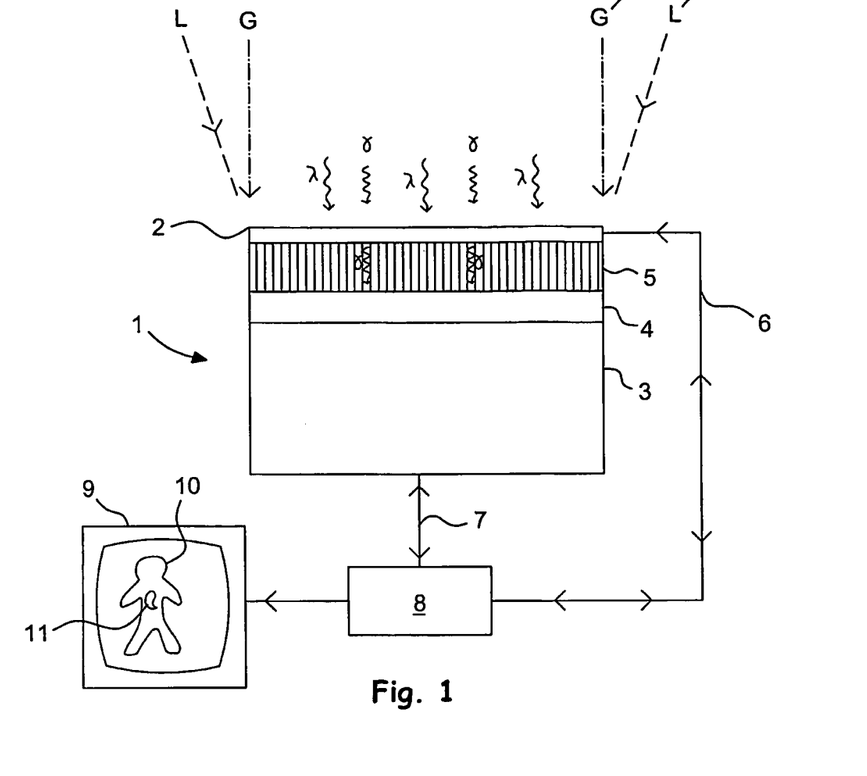
FIG. 1 schematically illustrates an imaging device for imaging using both light and gamma radiation simultaneously for imaging a common scene.

FIG. 1 schematically illustrates an imaging device for imaging a subject using both visible light ($\lambda$) and gamma rays ($\gamma$) simultaneously emanating from the subject. The device includes a camera unit (1) including a first sensor (2) responsive to light ($\lambda$) received by it from the subject, to generate first electrical camera unit signals (6) for use in forming a first image of the subject as seen in visible light. The camera unit also includes a second sensor responsive to gamma rays ($\gamma$) from the subject, to generate second camera unit electrical signals (7) for use in informing a second image of the subject as viewed with gamma rays.

The second sensor unit includes a silicon Charged Device (CCD) sensor unit (3) including an array of solid-state photo-sensitive pixel sensors (not shown) each of which is responsive to scintillation radiation to produce the second camera unit electrical signals (7). The second sensor unit also includes a scintillator layer formed from a polycrystalline material placed in direct contact with the photo-sensor array of the CCD unit (3). The thickness of the scintillator layer is greater than 200 μm, preferably greater than 400 μm and most preferably about 500 μm. The scintillator layer is responsive to incident gamma rays (γ) by scintillation, and the CCD unit (3) with which it is in direct contact is responsive to such scintillation radiation.

In using a relatively thick layer of polycrystalline scintillator material which is in direct contact with the CCD (or CMOS in other embodiments) pixel sensor array of the CCD device (3), high gamma ray count rates are achievable. This permits high energy resolution to be achieved over the gamma ray energy range of about 30-160 keV (or thereabouts). The scintillator layer (4) may be directly coated onto the CCD unit (3). In alternative embodiments, in which the scintillator layer is not in direct contact with the CCD unit (3), the former may be bonded to the latter with or without the use of an intermediate bonding agent. The scintillator layer (4) may comprise a rare earth phosphor, which may comprise Gd, and may comprise $Gd_2O_2S$ units. The rare earth phosphors employed in the scintillator layer may be $Gd_2O_2S(Tb)$ or $Gd_2O_2S(Pr, Ce, F)$. The scintillator layer may include CsI.

A collimator unit (5) is arranged to extend across the photo-sensitive pixel sensor array (not shown) of the CCD unit (3) and across an opposing face of the scintillator layer (4), such that the scintillator layer is effectively sandwiched between the collimator unit (5) and the CCD unit (3). The collimator unit (5) may be placed in contact with (e.g. bonded to) the scintillator layer (4), of may be separate from or separable from the scintillator layer.

Figure 2:
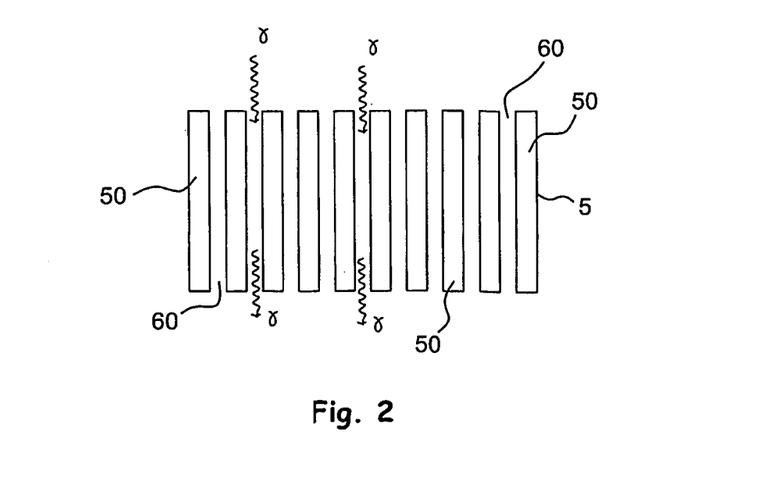
FIG. 2 schematically illustrates a collimator means for collimating gamma radiation.

The collimator unit (5) comprises an array of a multitude of parallel side-by-side tubular radiation conduits or apertures (60) disposed over the scintillator layer (4) and formed as an array of closely spaced perforations extending through the body (50) of the collimator unit as is shown in cross-section in FIG. 2. The material of the body of the collimator unit is substantially opaque to gamma rays incident upon it in use while being transparent to such gamma rays incident upon it along a propagation trajectory passing along a radiation conduit or perforation (60) formed therein. In this way, only gamma radiation propagating along a path parallel with the axis with which each of the radiation conduits (60) is commonly parallel, and intersecting such a conduit, is able to traverse through the collimator unit (5) from one perforated side thereof to the other perforated side. The collimator unit is arranged such that gamma rays having a propagation path enabling them to traverse the collimator unit unimpeded as discussed above also have a propagation path which subsequently intercepts the scintillator layer (4).

Consequently, the size of the apertures (60) of the radiation conduits of the collimator unit, together with the length of each radiation conduit, determines the spatial resolution and the effective "field of vision" of the second sensor unit (items 3, 4 and 5 in combination). This field of vision is schematically illustrated in FIG. 1 using peripheral gamma ray propagation trajectories G and G' delimiting the field of view of the camera unit (1) as viewed via gamma rays. Typically, collimators having apertures of about 500 μm diameter are preferable, however, it is possible to use apertures of larger or smaller diameter if desired. The collimator unit (5) may be fixed or may be detachable. In the latter case, one may provide a single camera unit having a plurality of different collimator units having radiation conduits/perforations of different aperture diameters, and/or of different conduit length (i.e. collimator thickness). This enables variable control over not only the spatial resolution of the camera unit, but also (or separately) over the degree of collimation and therefore the "field of view" of a camera unit using gamma rays.

Figure 3:
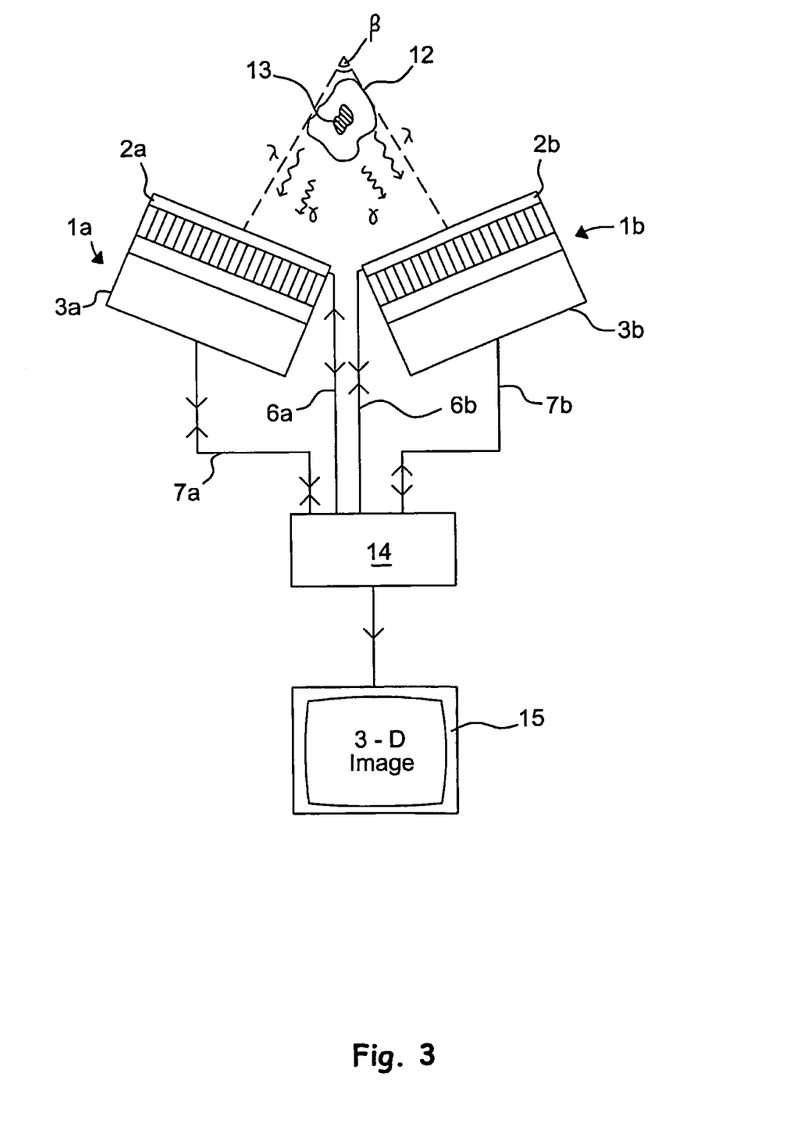
FIG. 3 schematically illustrates a stereoscope including a pair of imaging devices of the type illustrated in FIG. 1 each one of which is positioned to image a field of view offset by the field of view of the other of the pair by a predetermined parallax.
Figure 5A:
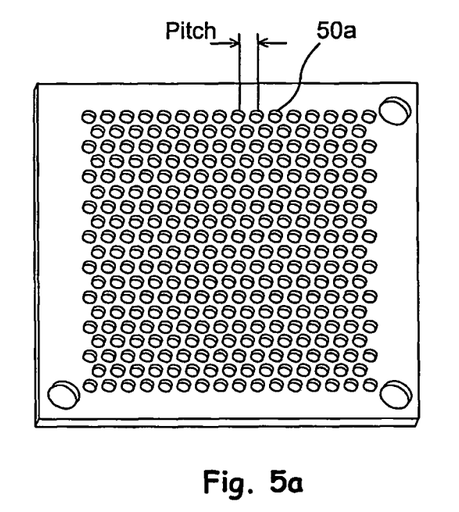
FIGS. 5A and 5B illustrate a high-resolution collimator and a high-sensitivity collimator respectively.
Figure 5B:
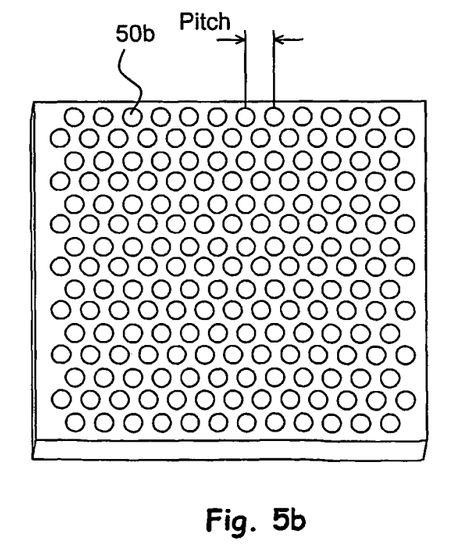

FIG. 5 illustrates two types of collimator suitable for use in the device illustrated in FIGS. 1 and 3.

The two varieties of collimator (5A, 5B) each comprise sheet gamma-ray absorbent Lead (Pb) into which extends an array of parallel collimation holes or channels passing from one side of the sheet through to an opposite side thereof through which gamma-rays may pass unimpeded. The thickness of the sheet is selected such that gamma-rays impinging upon a part of the collimator are substantially impeded (e.g., scattered or absorbed) thereby. Thus, gamma-rays not propagating through a hole or channel in a direction substantially or approximately parallel to the axis of the hole/channel will be filtered from the gamma-rays reaching the sensor array of the second sensor means.

For example, the collimator of FIG. 5A is a "high spatial resolution" collimator manufactured from seven 2.7 mm Pb sheets, each sheet having a hexagonal array of 1 mm diameter holes (50A) on 1.3 mm pitch, giving an overall thickness of 19 mm.

The "imaging" area is 20 mm×20 mm. This type of arrangement is found to produce gamma-ray images of relatively high spatial resolution due to the high density and small gauge of collimation channels.

The "high sensitivity" collimator of FIG. 5B was fabricated from four 5 mm Pb sheets (overall thickness of 20 mm) and has a hexagonal array of 2 mm diameter holes (50B) on 2.5 mm pitch. This type of arrangement is found to produce gamma-ray images from sources of relatively low intensity due to the higher aperture of the collimation channels.

Geometric sensitivities are $1.18\times10^{-4}$ and $1.27\times10^{-2}$ for the high spatial resolution and the high sensitivity collimator respectively.

A coded aperture mask may be used in addition to, or in place of, a collimator unit. The coded aperture mask may comprise an array or arrangement of apertures (e.g. circular, square or polygonal apertures) arrayed in a random or fixed pattern in a mask or plate. Such masks, as would be readily apparent to the person skilled in the art, permit three-dimensional mapping of the subject, imaged in gamma rays, by image reconstruction.

The first sensor unit (2) is positioned over the collimator unit (5) such that each of the outwardly presented apertures of the radiation conduits (60) of the collimator unit, which are presented towards the first imaging unit (2) and the subject being imaged in use, is covered by a part of the photo-sensing pixel array of the first imaging unit.

The first sensor unit may be connected to, or attached to (e.g. bonded) the collimator unit, and/or may be separable from, or separated from, the collimator unit. In the present example, the first sensor unit is mechanically detachably attached to the to the collimator unit.

The first sensor unit is dimensioned and arranged to be substantially fully transparent to gamma radiation incident upon it along a propagation path substantially parallel with the collimation axis of radiation conduits of the underlying collimator unit (5). The first sensor device is a thin CCD or MOS-type device fabricated from Silicon. As a result, the second sensor means is able to "view" the subject using gamma rays from substantially the same view point/position (no parallax) as the "view" of the subject seen by the first sensor means using light. This may be achieved without obscuration of the view of the second sensor by the presence of the first sensor in the field of vision of the second sensor.

Any "hot" pixels arising in the first image (produced by the first sensor means) as a result of gamma ray collisions with sensor elements of the first sensor means (e.g. CCD pixels) will typically should be small due to the suitable thinness of the first sensor means. In practice the user, or the control unit of the device, may check the first image for hot pixels, or the image data corresponding to hot pixels, and account/adjust the image data to remove the image artifacts resulting from them e.g. using suitable software.

The field of vision of the first sensor is delimited by the propagation trajectories of peripheral light rays L-L', and is arranged to fully include the field of vision of the second sensor (G-G'). This arrangement ensures that the boundaries of image of the visible surface of the imaged subject will fully enclose the boundaries concurrent image of the subject seen with gamma rays such that the relative position of the latter may be readily apparent by from the surrounding peripheral parts of the former when both are view concurrently in a composite image.

The device may include a "shroud" or "tube" (not shown) arranged to delimit the field of vision of either or both of the first and second sensors as necessary.

The imaging device includes a control unit (8) for controlling the first and second sensors to simultaneously generate respective first and second signals camera unit electrical signals (6 and 7 respectively) in response to concurrent light and gamma rays from the subject being imaged.

The control unit also includes a signal processing unit (not shown) arranged to receive and inputs both the first and second camera unit electrical signals (6 and 7 respectively) generated by the first and second sensors (2 and 3 respectively), and to generate image data therefrom.

The signal processing unit (8) is configurable to operate the CCD (3) of the second sensor unit in a photon counting mode to generate the second camera unit electrical signals (7) signal.

The signal processing unit is arranged to generate first image data representing an image of the view of the subject as "seen" by the first sensor in visible light, and to generate second image data representing the same view of the subject as "seen" by the second image sensor with gamma rays. The signal processing unit is configurable to generate image data from the concurrent first and second data signals representing an image composite (10, 11) of both the image of the subject according to light (10) and concurrently according to gamma radiation (11); The control unit (8) has an image data signal output port operably connected to the signal input of an image display device (e.g. a Visual Display Unit (VDU), television etc) responsive to the image data signal received from the control unit to generate an image according to the image data, thereby to display a composite image of the concurrent superimposed visible and gamma ray "views" of the imaged subject from the same viewpoint.

Figure 4:
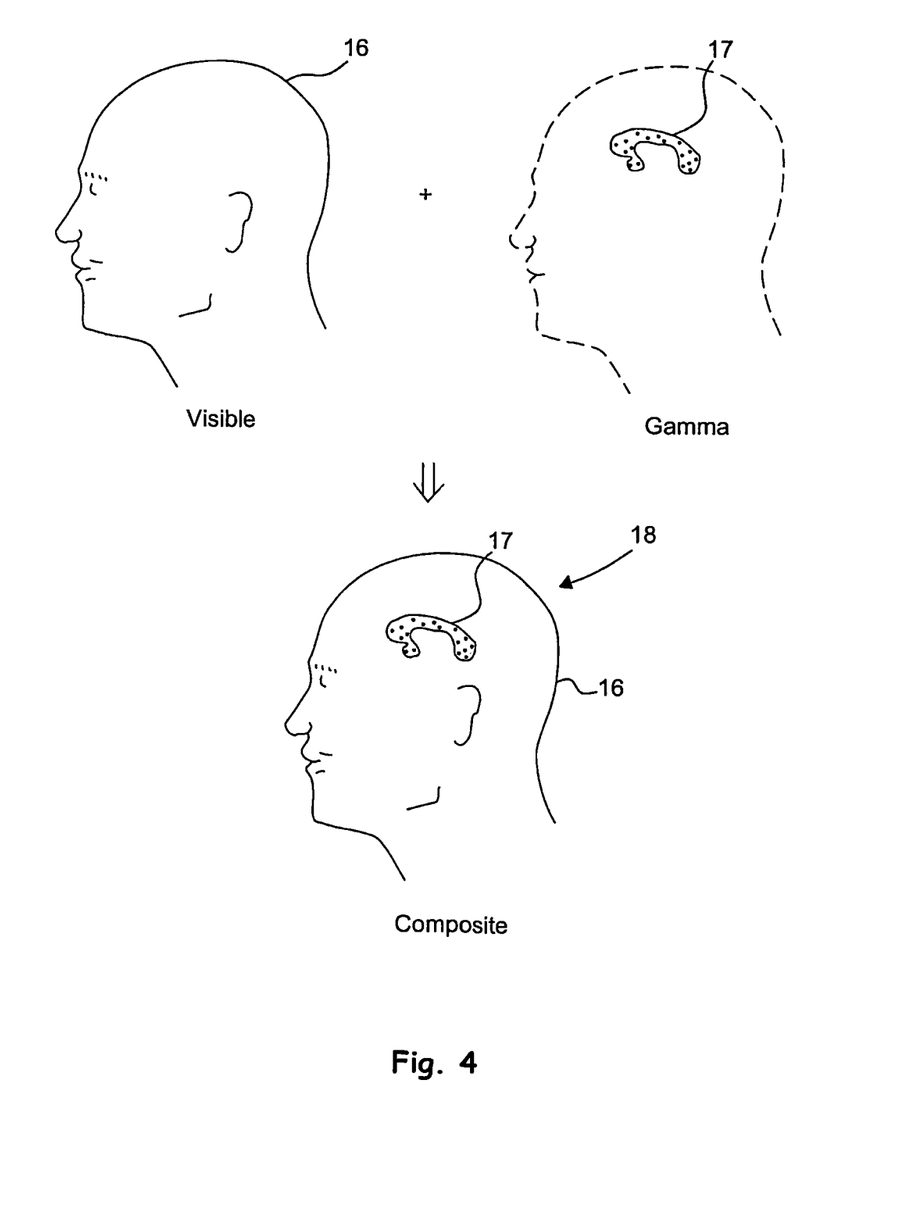

FIG. 4 schematically illustrates a further example of the superimposition of a light view image (16) and gamma ray view image (17) of a subject (a patient's head) which the signal processing unit of the control unit (8) is operable to generate image data representing, and to generate image data representing a superimposed composite image (18) comprising both. The visible image of the patient's head, generated using light, provides a view of the surface of the patient, while the gamma image, generated using concurrent gamma rays, provides a view of a hidden internal tracer-bearing organ of the patient emitting gamma rays. Both the visible view (16) and the gamma view (17) are concurrent views from the same viewpoint with no parallax between the two views. The signal processing unit is operable to generate from the image data of both the visible view with the gamma view, composite image data representing a superposition (18) of the two views, aligned to correctly represent the common viewpoint.

FIG. 3 schematically illustrates a stereoscope for use in imaging a subject stereoscopically including a first camera unit (1A) and a separate second camera unit (1B) each being substantially as described above with reference to FIG. 1 for concurrently imaging a common subject. The components of each of the first and second camera units if FIG. 3 include a respective first sensor unit (2A, 2B) responsive to light, and a second sensor unit (3A, 3B) responsive to gamma rays, each being substantially the same as the first sensor unit (1) and second sensor units, respectively, described above with reference to FIG. 1.

The common field of vision of the first and second sensor units (2A, 3A) of the first camera unit (1A) differs from the concurrent common field of vision of the first and second sensor units (2B, 3B) of the second camera unit (1B) by a finite predetermined parallax angle ($\beta$). That is to say, the first and second camera units are relatively positioned to have different fields of vision giving different (but similar) off-set "views" of the common gamma ray emitting subject (13) being imaged thereby. Collimated gamma rays received by the second sensor of the first camera unit propagate along a trajectory subtending the parallax angle with the trajectory along which collimated gamma rays propagate to reach the second sensor of the second camera unit. Due to the co-alignment of the first sensor units (2A, 2B) of each of the two cameras with respect to respective second (gamma) sensors of the cameras, the result is a corresponding parallax of "views" of the common light subject (12) visible in light, as between the first and second cameras, and "seen" by the camera pair using light.

A control unit (14) is operable in respect of each camera of the pair of cameras as is described above with reference to FIG. 1. The control unit includes stereoscopy signal processing means arranged to generate image data signals from the concurrent first and second signals of both the first and second camera units representing a three-dimensional (3D) stereoscopic composite view of the image of the subject both according to light and concurrently according to gamma radiation, and to output the image data signals to a VDU (15) responsive to generate the 3D image view.

The geometry of the stereoscope cameras may be such that e.g., their baseline separation is about 6 cm, i.e. a separation similar to the inter-ocular separation of a human.

It is to be understood that the above embodiments are examples only and that modifications to them, such as would be readily apparent to the skilled person, may be made without departing from the scope of the present invention.

The invention claimed is:

1. A device for use in imaging a subject using both light from a subject and gamma rays emanating from a radioactive substance within the subject, the device including:
   a first sensor which includes a solid state pixel device responsive to light received thereby from the subject to generate first signals for use in forming a first image of the subject; and
   a second sensor responsive to gamma rays received thereby from the subject to generate second signals for use in forming a second image of the subject and arranged to receive gamma rays from the subject which have passed from the subject through the first sensor before reaching the second sensor.

2. A device according to claim 1 wherein the first sensor is dimensioned and arranged to impart substantially no attenuation of gamma rays which are incident thereupon from the subject and propagating towards the second sensor in the field of vision thereof.

3. A device according to claim 1 in which the first sensor and the second sensor are arranged to receive light and gamma rays, respectively, which propagate from the subject upon substantially coincident paths such that the first sensor has a field of vision at least a part of which corresponds with at least a part of the field of vision of the second sensor.

4. A device according to claim 1 in which both the first sensor and the second sensor have a field of vision wherein the second sensor and the first sensor are co-aligned so as to share substantially a common field of vision.

5. A device according to claim 1 in which the second sensor has a field of vision and an aperture delimiting the field of vision thereof, and the first sensor substantially covers the whole of the aperture.

6. A device according to claim 1 in which the first sensor is attached to the second sensor.

7. A device according to claim 1 including a collimation device arranged between the first sensor and the second sensor to collimate gamma rays which have passed from the subject through the first sensor before reaching the second sensor.

8. A device according to claim 1 in which the second sensor includes a solid-state pixel sensor device having pixel sensors responsive to the direct receipt of gamma rays to produce said second signals.

9. A device according to claim 1 in which the second sensor includes a scintillator device responsive to gamma rays from the object by scintillation, and a scintillation sensor arranged to generate said second signals in response to said scintillation.

10. A device according to claim 9 in which the second sensor includes a collimation device arranged between the first sensor and the scintillator device of the second sensor to collimate gamma rays which have passed from the subject through the first sensor before reaching the scintillation sensor of the second sensor.

11. A device according to claim 1 including a control that controls the first and second sensor to simultaneously generate respective first and second signals in response to concurrent light and gamma rays from said subject, and a signal processing device to generate image data from the concurrent first and second data signals representing an image composite of both the image of the subject according to light and concurrently according to gamma radiation.

12. A device according to claim 1 in which the second sensor includes a solid-state pixel sensor array, and a processing device arranged to receive an input from the pixel sensor array being configurable to operate in a photon counting mode to generate said second signal according to said input.

13. A stereoscope for use in imaging a subject stereoscopically including:
a first device according to claim 1 for imaging the subject;
a second device according to claim 1 for imaging the subject concurrently with the first device being separate from the first device and arranged such that the field of vision of the second sensor of the second device differs from the concurrent field of vision of the second sensor of the first device by a finite predetermined parallax;
signal processing device to generate image data from the concurrent first and second signals of both the first and second device representing a three-dimensional (3D) stereoscopic composite view of the image of the subject both according to light and concurrently according to gamma radiation.

14. A method of imaging a subject using both light from the subject and gamma rays emanating from a radioactive substance within the subject, the method including:
detecting light from the subject with a first sensor and therewith generating first signals for use in forming a first image of the subject; and
detecting with a second sensor gamma rays from the subject which have passed from the subject through the first sensor before reaching the second sensor and therewith generating second signals for use in forming an image second image of the subject.

15. A method according to claim 14 including arranging the first sensor and the second sensor to receive light and gamma rays, respectively, which propagate from the subject concurrently upon substantially coincident paths such that the first sensor has a field of vision at least a part of which corresponds with at least a part of the field of vision of the second sensor.

16. A method according to claim 14 including co-aligning the first and second sensor so as to share substantially a common field of vision.

17. A method according to claim 14 including providing the second sensor with an aperture delimiting the field of vision thereof, and substantially covering the whole of the aperture with the first sensor.

18. A method according to claim 14 in which the first sensor is attached to the second sensor.

19. A method according to claim 14 including detecting said gamma rays with the second sensor by generating said second signals in response to the direct receipt of gamma rays by solid-state pixel sensors of the second sensor.

20. A method according to claim 14 including detecting said gamma rays with said second sensor by detecting scintillations within a scintillator device thereof responsive to gamma rays from the object by scintillation, and generating said second signals in response to said scintillation.

21. A method according to claim 14 including collimating gamma rays which have passed from the subject through the first sensor before being detected by the second sensor.

22. A method according to claim 14 including controlling the first and second sensor to generate respective first and second signals in response to light and gamma rays from said subject, and generating image data from the first and second data signals representing an image composite of the image of the subject both according to light and concurrently according to gamma radiation.

23. A method of imaging a subject stereoscopically including:
in a first step generating said first and second signals according to the method of claim 14 for imaging the subject;
in a second step generating said first and second signals according to the method of claim 14 for imaging the subject such that the field of vision of the image associated with of the second step differs from the field of vision of the image associated with the first step by a finite predetermined parallax; and
generating image data from the first and second signals generated in both the first and second steps representing a three-dimensional (3D) stereoscopic composite view of the image of the subject both according to light and concurrently according to gamma radiation.

* * * * *